United States Patent
Collin et al.

(10) Patent No.: US 6,541,519 B2
(45) Date of Patent: Apr. 1, 2003

(54) METHODS AND COMPOSITIONS FOR TREATING LIPOXYGENASE-MEDIATED DISEASE STATES

(75) Inventors: Peter D. Collin, Sunset, ME (US); Peiying Yang, Missouri City, TX (US); Robert Newman, Sugarland, TX (US)

(73) Assignee: Coastside Bio Resources, Stonington, ME (US)

( * ) Notice: Subject to any disclaimer, the term of this patent is extended or adjusted under 35 U.S.C. 154(b) by 0 days.

(21) Appl. No.: 09/827,361

(22) Filed: Apr. 6, 2001

(65) Prior Publication Data

US 2002/0013368 A1 Jan. 31, 2002

Related U.S. Application Data

(60) Provisional application No. 60/194,863, filed on Apr. 6, 2000.

(51) Int. Cl.$^7$ .............. A61K 31/20; A61K 31/202; A61K 35/12; A61K 35/60; A61K 35/24

(52) U.S. Cl. .............. 514/558; 514/536; 514/824; 514/946; 424/572; 424/574; 424/450; 424/522; 424/523; 424/537

(58) Field of Search ................ 514/558, 536, 514/824, 946; 424/574, 450, 522, 523, 537, 572

(56) References Cited

U.S. PATENT DOCUMENTS 6,214,875 B1    6/2001   Yang

OTHER PUBLICATIONS

Derwent Accession No.:1988–297307, Enhancing anti–cancer activity . . . , Nippon Oils & Fats Co Tld, JP 63218623 a, Sep. 12, 1988, abstract.*

* cited by examiner

Primary Examiner—Frederick Krass
Assistant Examiner—Clinton Ostrup
(74) Attorney, Agent, or Firm—Rothwell, Figg, Ernst & Manbeck

(57) ABSTRACT

Methods and compositions are disclosed for prevention and/or treatment of diseases in which 5- and 12-lipoxygenase activity contributes to the pathological condition, by administration of 12-methyltradecanoic acids alone and in conjunction with other therapeutic compounds. Methods to inhibit lipoxygenase-mediated inflammations are disclosed.

2 Claims, 3 Drawing Sheets

METHODS AND COMPOSITIONS FOR TREATING LIPOXYGENASE-MEDIATED DISEASE STATES

This application claims the benefit of U.S. Provisional Application No. 60/194,863, filed Apr. 6, 2000.

FIELD OF THE INVENTION

The present invention relates to the use of 12-methyltetradecanoic acid which can kill tumor cells by inducing cell apoptosis related to inhibition of 5-lipoxygenase metabolites and 12-lipoxygenase metabolites or their related activities in various mammalian cancers. In particular, the present invention relates to the methods using 12-methyltetradecanoic acid (12-MTA) alone or in combination with other anti-cancer compounds that are targeted to inhibit cancer progression in a mammal by inducing tumor cell apoptosis.

DESCRIPTION OF RELATED ART

Normal tissue homeostasis is maintained by balanced cell proliferation and cell death, which occurs most frequently in the form of apoptosis or programmed cell death. Tumor cells differ significantly from their normal counterparts with respect to the control of cell growth and proliferation. Most tumor cells demonstrate a self-dominant growth pattern either due to their abnormal response to environmental stimuli (hormones, growth factors, cytokines, etc.) or due to an autonomous nature of growth (i.e., autocrine stimulation). Tumor cells also demonstrate abnormal apoptotic responses. Many factors have been shown to regulate apoptosis, including (i) growth factors and growth factor receptors such as retinoid acid, interleukin-3, stem cell factor, interferon-γ, erythropoietin, NGF/NGF (nerve growth factor) receptor, TNF-α/Fas (tumor necrosis factor-α), steel factor/Kit receptor, TGF-β/TGF (transforming growth factor) receptor, insulin, EGF/EGFR (epidermal growth factor), IGF-1/IGF (insulin-like growth factor) receptor, and PDGF/PDGF (platelet-derived growth factor receptor); (ii) intracellular signal transducers such as protein kinase C, PI-3 (phosphoinositol-3) kinase, Ras and GTPase, PLC-γ (phospholipase C-γ), tyrosine kinases and protein phosphatases, lipid signaling molecules such as eicosanoids, sphingosine, ceramide, and $Ca^{2+}$; (iii) cell cycle regulators exemplified by Cdc-2 and E2F-1; (iv) reactive oxygen species or other free radicals; (v) extracellular matrix regulators/cell adhesion molecules (extracellular matrix proteins such as fibronectin and transmembrane integrin receptors); and (vi) specific endonucleases such as $Ca^{2+}$- and $Mg^{2+}$-dependent DNase and cytoplasmic proteases typified by ICE (interleukin 1β-converting enzyme) family. Many of these regulators have been associated with various human malignancies and apoptosis. For example, studies on human tumors including neuroblastoma, glioma, lymphoma, breast carcinoma, colorectal adenocarcinoma, melanoma and gastrointestinal malignancies have demonstrated an overall positive correlation between increased expression of Bcl-2 (or Bcl-$X_L$) or decreased expression of Bax and uncontrolled tumor cell growth, and, in some cases, with tumor progression and a poor prognosis of cancer patients. Another example is p53, a phosphoprotein known to modulate gene transcription, police cell cycle checkpoints, control DNA replication and repair, and maintain genomic stability. Wild type p53 also positively regulates apoptosis. p53 gene mutations have been linked to attenuated apoptosis in multiple cancers represented by Wilms' tumor, colon cancer, cervical carcinoma and breast cancer. Since apoptosis plays a critical role in multiple steps (transformation, progression and survival of metastases) of tumorigenesis as well as in tumor cells' response to chemotherapeutic drugs or radiation therapy, many chemoprevention and therapeutic regimens attempting to manipulate apoptotic process have been proposed to aid in the clinical treatment of cancer patients (Fesus, L., et al., J. Cell Biochem. 22:151–161 (1995); Lotan, R., J. Natl. Cancer Inst. 87:1655–1657 (1995); van Zandwijk, N., J. Cell Biochem. 22:24–32 (1995)).

Arachidonic acid (AA) is an essential component of the cell membrane phospholipids. AA released through the action of phospholipase $A_2$ is metabolized via three major biochemical pathways: (i) the cyclooxygenase (COX) pathway leading to the generation of prostaglandins, prostacyclin, and thromboxane; (ii) the lipoxygenase (LOX) pathway giving rise to various hydroperoxy (HPETEs) and hydroxy (HETEs) fatty acids as well as leukotrienes; and (iii) the P450-dependent epoxygenase pathway generating EETs. Mammalian LOX display varying degrees of substrate specificity for insertion of molecular oxygen into arachidonic acid at carbon positions 5, 12, and 15. The enzymes, based on the abundance of the majority products have thus been termed 5, 12, and 15 lipoxygenases, respectively. The 12-LOX catalyzes the transformation of AA into 12(S)-hydroperoxyeicosatetraenoic acid (12-HPETE) and its 12(S)-hydroxy derivatives, i.e., 12(S)-hydroxyeicosatetraenoic acid (12(S)-HETE). Three types of mammalian 12-LOX enzymes have so far been reported. The first is human platelet-type 12-lipoxygenase expressed normally in platelets, HEL (human erythroleukemia) cells, and umbilical vein endothelial cells (Funk, C. D., et al., Proc. Natl. Acad. Sci. 87:5638–5642 (1990); Funk, C. D., et al., Proc. Natl. Acad. Sci. 89:3962–3966 (1992)). Platelet-type 12-LOX metabolizes only AA (but not C-18 fatty acids such as linoleic acid) to form exclusively 12(S)-HETE (Funk, C. D., et al., Proc. Natl. Acad. Sci. 87:5638–5642 (1990) Marnett, L. J., et al., Adv. Prostaglandin Thromboxane Leukotriene Res. 21:895–900 (1990)). The second is porcine leukocyte-type 12-LOX which metabolizes both AA and linoleic acid thus generating 12(S)-HETE as well as small amounts of 15(S)-HETE (Hada, T., et al., Biochim. Biophys. Acta 1083–1087 (1991)). The third type of 12-LOX (sometimes termed epithelial 12-lipoxygenase) has been isolated from bovine tracheal epithelial cells (De Marzo, N., et al., J. Physiol. 262:L198-L207 (1992)); rat brain (Watanabe, S., et al., Eur. J. Biochem. 212:605–612 (1993)), and murine macrophages (Freier-Moar, J., et al., Biochim. Biophys. Acta., 1254:112–116 (1995)), which shares more homology with 15-LOX and leukocyte-type 12-LOX than with platelet-type 12-LOX. This type of 12-LOX, like reticulocyte 15-LOX and leukocyte-type 12-LOX, catalyzes the formation of both 12(S)-HETE and 15(S)-HETE.

The role of AA metabolites in regulating cell proliferation has been recognized for more than two decades. Numerous studies have demonstrated a strong positive correlation between growth factor—(EGF, insulin, PDGF, etc.) promoted cell proliferation and generation of various COX products, primarily prostaglandins (Skouteris, G. G., et al., Biochem. Biophys. Res. Commun., 178:1240–1246 (1991); Nolan, R. D., et al., Mol. Pharmacol. 33:650–656 (1988); Smith, D. L., et al., Prostaglandins Leukotrienes Med., 16:1–10 (1984)). Similarly, it has been found that various eicosanoids derived from LOX pathways as well as epoxygenase pathways of AA metabolism play an essential role in mediating the growth factor-stimulated normal cell and tumor cell growth. Examples include 15-HETE as a mitogenic regulator of T-lymphocyte (Bailey, J. M., et al., Cell Immunol., 67:112–120 (1982)), 12-HETE and LTB.sub.4 as growth stimulators of epidermal cells (Chan, C., et al., J. Invest. Dermatol., 85:333–334 (1985)), 12-HETE stimulation of keratinocyte DNA synthesis (Kragballe, K., et al., Arch. Dermatol. Res., 278:449–453 (1986)), 15-/12-HETEs as mediators of insulin and EGF-stimulated mammary epithelial cell proliferation (Bandyopadhyay, G. K., et al., J. Biol. Chem., 263:7567–7573 (1988)) and as synergistic effectors of bFGF—(basic fibroblast growth factor) and PDGF-regulated growth of vascular endothelial cells and smooth muscle cells (Yamaja Setty, B. N., et al., J. Biol. Chem., 262:17613–17622 (1987); Dethlefsen, S. M., et al., Exp. Cell Res., 212:262–273 (1994)), 12(S)-HETE as a regulator of EGF- and insulin-stimulated DNA synthesis and protooncogene expression in lens epithelial cells (Lysz, T. W., et al., Cell Growth & Differ., 5:1069–1076 (1994)) and as the mediator of angiotensin II-induced aldosterone synthesis in adrenal glomerulosa cells (Nadler, R. D., et al., J. Clin. Invest., 80:1763–1769 (1987)).

Early work demonstrated an important function for prostacyclin ($PGI_2$) and thromboxane ($TxA_2$), two major cyclooxygenase (COX) products of AA metabolism derived primarily from vascular endothelial cells and platelets, respectively, in regulating the hematogenous spreading of malignant tumor cells, reviewed in Schneider et al., Cancer metastasis Rev. 13:349–364 (1994). Later, systematic in vitro and in vivo studies have led to the discovery that many LOX metabolites also play a key role in modulating the phenotypic properties of tumor cells as well as tumor cell-vasculature interactions (Reviewed in Cancer Metastasis Rev. 11:353–375 (1992); Prominently, a small hydroxy fatty acid molecule derived from the LOX pathway of AA metabolism, i.e., 12(S)-HETE, has been observed to possess a wide-spectrum of biological activities including, among others, inducing platelet aggregation, stimulating insulin secretion, suppressing renin production, chemoattracting leukocytes, facilitating macrophage adhesion, inhibiting prostacyclin biosynthesis by vascular endothelial cells (Spector, A. A., et al., Prog. Lipid Res. 27:271–323 (1988); Sekiya, K., et al., Biochem. Biophys. Res. Commun. 105:1090–1095 (1982), modulating tumor cell interactions with extracellular matrix, promoting tumor cell motility, facilitating tumor cell release of proteolytic enzyme cathepsin B, reorganizing tumor cell cytoskeleton, promoting tumor cell adhesion on endothelial cells via upregulating integrin expression on tumor cells and/or endothelial cells, and inducing endothelial cell retraction thus enhancing tumor cell extravasation from the vasculature (reviewed in Seminar Thromb. Hemost. 18:390–413 (1992); Cancer Metastasis Rev., 13:365–396 (1994); Annals New York Acad. Sci., 744:199–215 (1994); Invasion Metastasis 14:109–122 (1995). Significant progress has been made in delineating the molecular mechanisms of the 12(S)-HETE effects. 12(S)-HETE, possibly through binding to a cell surface receptor(s), triggers phosphoinositol lipid hydrolysis (Liu, B., et al., Proc. Natl. Acad. Sci. 92:9323–9327 (1995)) leading to the intracellular activation of protein kinase C (PKC; Liu, B., et al., Cell Regul. 2:1045–1055 (1992)) and/or protein tyrosine kinase (PTK; Tang, D. G., et al., J. Cell. Physiol. 165:291–306 (1995c)). The interactions of these phosphorylated protein kinases with various intracellular molecular targets (e.g., cytoskeletal proteins, adhesion molecules, signaling molecules, etc.) largely explain the versatility of the 12(S)-HETE effects.

Both COX and LOX products of AA metabolism may also be involved in modulating tumor cell survival and apoptosis. Thus, many prostaglandins such as $PGE_2$ (prostaglandin $E_2$) (Brown, D. M., et al., Clin. Immunol. Immunopathol. 63:221–229 (1992)), $PGA_2$ and $\Delta^{12}$-$PGJ_2$ (Kim, I-K, et al., FEBS Lett. 312:209–214 (1993)) have been shown to induce apoptosis of leukemia or lymphoma cells as well as solid tumor cells. Similarly, $TxA_2$ induces apoptotic cell death of immature thymocytes by binding to the cell surface $TxA_2$ receptors (Ushikubi, F., et al., J. Exp. Med. 178:1825–1830 (1993)). Interestingly, $PGE_2$ also has been reported to protect cells from apoptosis induction (Goetzel, E. J., et al., J. Immunol. 154:1041–1047 (1995)). On the other hand, various COX inhibitors (NSAID) (Non-steroidal anti-inflammation drugs) have been consistently demonstrated to trigger apoptosis of cultured cells. Thus, indomethacin, sulindac sulfide and sulfone inhibit colon carcinoma cell (HT-29) growth by inducing apoptosis (Shiff, S. J., et al., J. Clin. Invest. 96:491–503 (1995); Piazza, G. A., et al., Cancer Res. 55:3110–3116 (1995); Shiff, S. J., et al., Exp. Cell Res. 222:179–188 (1996)). Likewise, multiple NSAIDs including diflunisal, indomethacin, acemethacin, diclofenac, mefenamic acid, flufenamic acid, niflumic acid, ibuprofen, and carprofen cause apoptosis in chicken embryo fibroblasts (Lu, X., et al., Proc. Natl. Acad. Sci. 92:7961–7965 (1995)). These observations suggest that the COX/COX metabolites may play a dual role in regulating cell survival and apoptosis. Under certain circumstances the COX products (e.g., $PGE_2$ and cyclopentenone prostaglandins) can either directly trigger cell death or mediate apoptosis induced by, e.g., TNF-α (Larrick, J. W., and S. C. Wright, FASEB J. 4:3215–3223 (1990)). In a different scenario, the COX activity/function are critical for cell survival since inhibition with various inhibitors leads to cell death (see above). Consistent with this, overexpression of COX-2 has been observed to confer resistance in rat intestinal epithelial cells to apoptosis induction by butyrate (Tsujii, M., and R. DuBois, Cell 83:493–501 (1995)).

Similar to the COX system, some LOXs and their products may also play a dual regulatory role in cell survival and apoptosis. Exogenous lipid hydroperoxides such as 15-HPETE induces HIV-infected human T cells (Sandstrom, et al., J. Biol. Chem. 269:798–802 (1994)) due to their inability to convert 15-HPETE to 15-HETE owing to a reduction in the glutathione peroxidase activity, LOX metabolites have been proposed as the actual mediators of TNFα-induced apoptosis of multiple cells since LOX inhibitors such as ETYA and NDGA could inhibit its cytotoxicity (Chang, D. J., et al., Biochem. Biophys. Res. Commun. 188:538–546 (1992); O'Donell, V. B., et al., Biochem. J. 310:133–141 (1995)). On the other hand, 5-LOX inhibitors can cause apoptosis of human leukemia blast cells (Anderson, K. M., et al., Prosta. Leuko. Essent. Fat. Acids 48:323–326 (1993)) and interruption of 5-LOX-mediated growth factor signaling inhibits the growth of lung cancer cells due to apoptosis induction (Avis, I. M., et al., J. Clin. Invest. 97:806–813 (1996)), suggesting that in some cells the 5-LOX pathway may function as a critical survival factor.

Inflammation inhibition via inhibition of lipoxygenases in mammals is also an aspect of the background of the present invention. Lipoxygenases are involved in several mammalian inflammatory pathologies such as psoriasis, asthma, atopic dermatitis, arthritis, Crohn's Disease, irritable bowel syndrome and others.

Japanese patent application JP 7002661A describes 12-MTA as being an inhibitor of myeloperoxidase secretion from polymorphonuclear leukocytes. The patent application does not describe 12-MTA as an inhibitor of lipoxygenase nor of cancer cell growth, or as an inducer of apoptosis in malignant cancer cells.

It has been shown by Collin (PCT/US99/01179) that lipids derived from sea cucumber, especially of the class *Cucumaria frondosa,* inhibit 5- and 12-lipoxygenase. Related to this lipoxygenase inhibition is the inhibition of inflammation in mammals, both systemically and topically. Surprisingly, it was found by the present inventors that one compound isolated from *Cucumaria frondosa,* 12-MTA, is a dramatic inhibitor of lipoxygenases and a dramatic inhibitor of various cancer cell proliferation in vitro.

Inhibition of various lipoxygenase activities in cancer victims or for prevention of cancers, through administration of lipoxygenase inhibitors is a promising therapy for humans and animals. Currently, no lipoxygenase inhibitors have been approved for general anti-cancer therapies.

SUMMARY OF THE INVENTION

It is therefore an object of the present invention to provide a method for the inhibition of cancer proliferation in humans and other animals by the administration of 12-MTA or 12-MTA in combination with other nutritional or anti-cancer compounds, either topically, orally, intraperitoneally or other means known to the medical arts.

It is as additional object of the present invention to provide a composition of matter consisting of 12-MTA derived from sea cucumber, preferably comprising 60% or more 12-MTA, between 10 and 20% palmitoleic acid, between 10 and 30% eicosapentaenoic acid (EPA), and less than 10% of other fatty acids, including myristic acid (14:0) and oleic acid (18:1), useful as an anti-inflammatory therapeutic product. Such a product is useful in inhibiting inflammation in a mammal by reducing the expression of lipoxygenase activities, especially in conjunction with other anti-inflammatory compounds which inhibit the cyclooxygenase cascade in vivo.

It is an additional object of the present invention that 12-MTA can be complexed with currently approved anti-cancer agents and that such a complexed compound will render some current drugs more efficacious. For example, gemcitabine esters or amides in which the 3' and/or 5' OH group and/or the N4-amino group are derivatised with 12-MTA, can be made by those skilled in the arts, thus making the complex more useful as an anti-cancer agent. Other anti-cancer compounds such as cyclophosphamide (alkylating agent), 5-fluorouracil (antimetabolite), etoposide (semisynthetic podophyllotoxin agent) and vincristine (vinca alkaloid) may be compounded with 12-MTA or administered separately by being spaced out over time in dosages that provide an effective amount of each synergistically.

The present invention also relates to combinations of 12-MTA with paclitaxel (Taxol®, Bristol Myers Squibb), docetaxel (Taxotere®. Rhone-Poulenc Rorer) and their analogues and substances which are therapeutically useful in the treatment of neoplastic diseases.

Taxol®, Taxotere® and their analogues, which possess noteworthy antitumor and antileukemic properties, are especially useful in the treatment of cancers of the ovary, breast or lung.

The preparation of Taxol®, Taxotere® and their derivatives form the subject, for example, of European Patents EP 0,253,738 and EP 0,253,739 and International Application PCT WO 92/09,589.

Generally, the doses used, which depend on factors distinctive to the subject to be treated, are between 1 and 10 mg/kg administered intraperitoneally or between 1 and 3 mg/kg administered intravenously.

Among substances which may be used in association or in combination with 12-MTA are: Taxol®, Taxotere® or their analogues, alkylating agents such as cyclophosphamide, isosfamide, melphalan, hexamethylmelamine, thiotepa or dacarbazine, antimetabolites such as pyrimidine analogues, for instance 5-fluorouracil and cytarabine or its analogues such as 2-fluorodeoxycytidine, or folic acid analogues such as methotrexate, idatrexate or trimetrexate, spindle poisons including vinca alkaloids such as vinblastine or vincristine or their synthetic analogues such as navelbine, or estramustine or taxoids, epidophylloptoxins such as etoposide or teniposide, antibiotics such as daunorubicine, doxorubicin, bleomycin or mitomycin, enzymes such as L-asparaginase, topoisomerase inhibitors such as camptothecin derivatives chosen from CPT-11 and topotecan or pyridobenzoindole derivatives, and various agents such as procarbazine, mitoxantrone, platinum coordination complexes such as cisplatin or carboplatin, and biological response modifiers or growth factor inhibitors such as interferons or interleukins.

It is also an object of the present invention to induce apoptosis of tumor cells in a mammal using 12-MTA and/or 12-MTA in combinations with other anti-cancer agents. Further, it is an object of the present invention to provide methods which can be effective in treating tumors. These and other objects will become increasingly apparent by reference to the following description and the drawings.

DETAILED DESCRIPTION OF THE INVENTION

Figure 1:
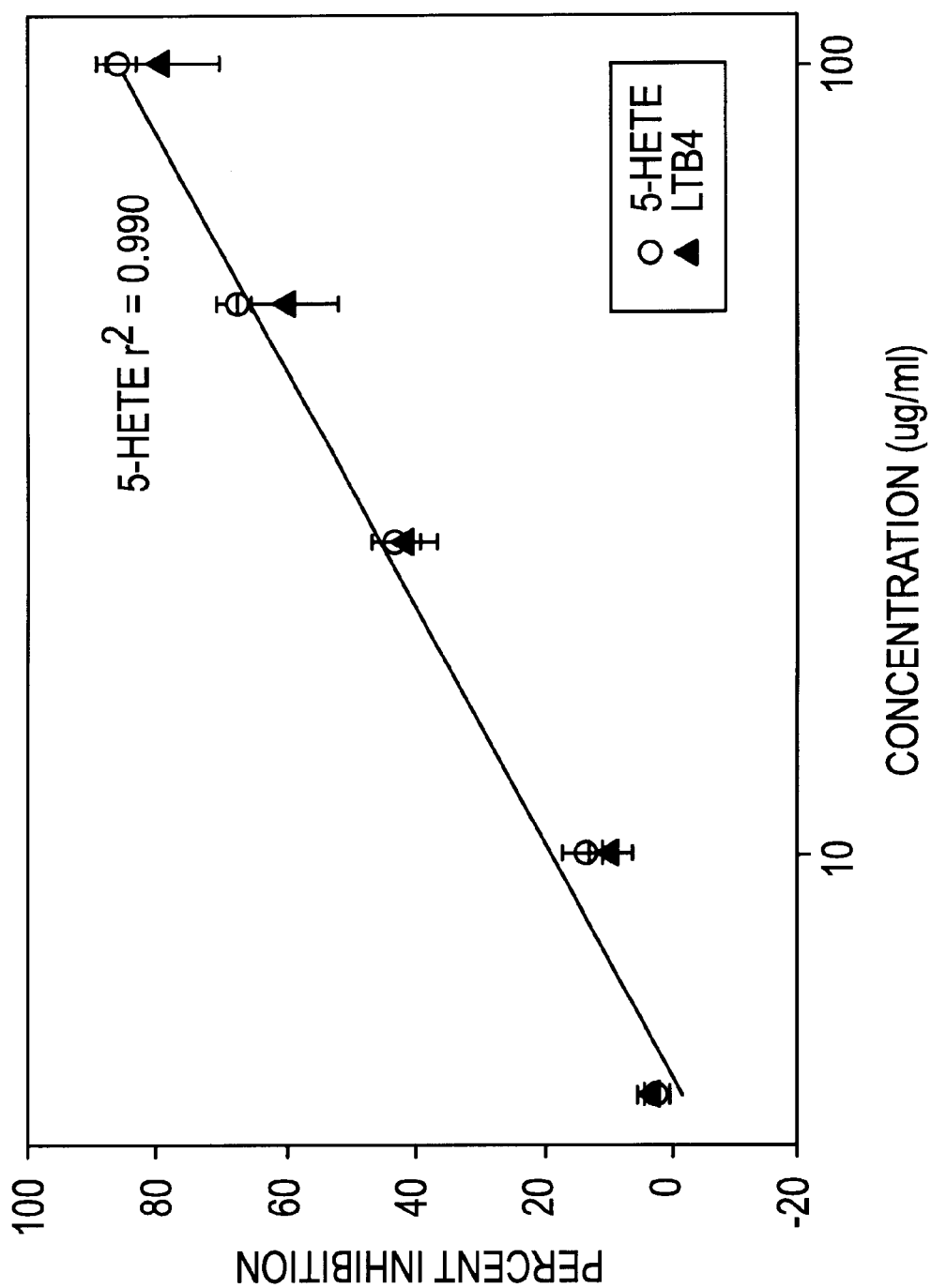
FIG. 1. Inhibitory effect of 12-MTA on production of 5-HETE and LTB4 in RBL-1 cells (n=3). Data are presented as mean +/− SD of three separated experiments.

In general, the current invention relates to inhibiting any disease in which 5- and/or 12-lipoxygenase, or their metabolites or the activities thereof, contribute to the pathological condition. It has been discovered by the current inventors that 12-MTA is a potent inhibitor of various lipoxygenases, and as such, can be utilized in anti-cancer and anti-inflammatory preparations in effective amounts, depending upon various parameters as are known to those skilled in the healing arts.

The present invention provides a method for treating or preventing a cancer in a subject in need of such treatment or prevention which comprises administering to the subject an amount of 12-MTA effective to treat or prevent a cancer. The present invention also provides a method for treating or preventing cancer in a subject in need of such treatment by administering an effective amount of 12-MTA. In vitro, 12-MTA is a potent inhibitor of 5-HETE (FIG. 1) and 12-HETE. Furthermore, 12-MTA has been shown to be a dramatic inhibitor of prostate cancer cell proliferation. The use of 12-MTA has been shown to induce apoptosis (programmed cell death) in cancer cells, making it a potent anti-cancer agent, either alone or in combination with other anti-cancer compounds.

The ability of the compounds of the present invention to inhibit lipoxygenase enzyme makes them useful for controlling the symptoms induced by the endogenous metabolites arising from arachidonic acid in a mammalian subject, especially a human subject. The compounds are therefore valuable in the prevention and treatment of such disease states in which the accumulation of arachidonic acid metabolites are the causative factor; e.g. allergic bronchial asthma, skin disorders, rheumatoid arthritis, cancers and osteoarthritis.

A particularly significant recent finding in this regard is that 5-lipoxygenase inhibitors and some leukotriene inhibitors protect the gastric mucosa against lesions induced by the oral or parenteral administration of most nonsteroidal anti-inflammatory drugs [see Rainsford, Agents and Actions, 21, 316–19 (1987)]. Accordingly, a significant body of evidence implicates the involvement of lipoxygenase products in the development of pathological features associated with gastric mucosal lesions, such as for example those induced by ethanol exposure and administration of nonsteroidal anti-inflammatory drugs. Thus, compounds which inhibit the biological effects of leukotrienes and/or which control the biosynthesis of these substances, as by inhibiting 5-lipoxygenase, are considered to be of value as cytoprotective agents. As a 5-lipoxygenase inhibitor, 12-MTA and/or 12-MTA in conjunction with other therapeutic co-factors can be a significant therapeutic agent for protecting the gastric mucosa against non-steroidal anti-inflammatory drugs.

For treatment of the various conditions described above, the 12-MTA compounds and their pharmaceutically acceptable salts can be administered to a human subject either alone, or preferably in combination with pharmaceutically acceptable carriers or diluents in a pharmaceutical composition according to standard pharmaceutical practice. The compounds can be administered orally or parenterally in conventional fashion.

When 12-MTA bearing compositions (in a preferred embodiment, compositions containing at least approximately 60% of 12-MTA) are administered to a human subject for the prevention or treatment of an inflammatory disease, the oral dose range will be from about 0.1 to 300 mg/kg per body weight of the subject to be treated per day, preferably from about 0.1 to 60 mg/kg per day, in single or divided doses. If parenteral administration is desired, then an effective dose will be from about 0.05 to 30 mg/kg per body weight of the subject to be treated per day. In some instances it may be necessary to use dosages outside these limits, since the dosages will necessarily vary according to the age, weight and response of the individual patient as well as the severity of the patient's symptoms and the percentage of 12-MTA incorporated in the dosage form and potency of the particular composition being administered.

For oral administration, the 12-MTA bearing compounds of the invention and their pharmaceutically acceptable salts can be administered, for example, in the form of tablets, powders, lozenges, syrups or capsules or as an aqueous solution or suspension. In the case of tablets for oral use, carriers which are commonly used include lactose and corn starch. Further lubricating agents such as magnesium stearate are commonly added. In the case of capsules, useful diluents are lactose and dried corn starch. When aqueous suspensions are required for oral use, the active ingredient is combined with emulsifying and suspending agents. If desired, certain sweetening and/or flavoring agents can be added. For intramuscular, intraperitoneal, subcutaneous and intravenous use, sterile solutions of the active ingredient are usually prepared and the pH of the solutions should be suitably adjusted and buffered. For intravenous use, the total concentration of solute should be controlled to make the preparation isotonic.

In addition, particularly for the treatment of asthma, the 12-MTA bearing compounds of this invention can be administered to a human subject by inhalation. For this purpose they are administered as a spray or mist, according to standard practice.

The term "treatment" includes partial or total inhibition of an inflammatory pathology and/or the cancer growth, as well as partial or total destruction of same.

The term "prevention" includes either preventing the onset of clinically evident cancer altogether or preventing the onset of a preclinically evident stage of cancer in individuals at risk, also intended to encompassed by this definition is the prevention of initiation for malignant cells or to arrest or reverse the progression of premalignant cells to malignant cells.

The term "subject" for purposes of treatment includes any human or animal subject who has any one of the known cancers, and preferably is a human subject. For methods of prevention, the subject is any human or animal subject, and preferably is a human subject who is at risk for obtaining a cancer. The subject may be at risk due to exposure to carcinogenic agents, being genetically predisposed to have the cancer, and the like.

Natural Sources of 12-MTA:

12-methyltetradecanoic acid has been found by the inventors to be a dramatic inhibitor of 5- and 12-lipoxygenase and was physically isolated from the lipid extract of *Cucumaria frondosa,* a patented (Collin, U.S. Pat. No. 6,055,936) extract known to exhibit anti-inflammatory and anti-cancer activity. The method of isolation was by 'activity based fractionation' using 5- and 12-lipoxygenase inhibition as the guiding assay. Using chromatography, preparative HPLC and preparative TLC of the sea cucumber oil, and checking 5-HETE with detection with UV at 235 nm, one particular spot on the TLC inhibited 5-HETE by approximately 94% at a 1:100 dilution. (FIGS. 3 and 4) The effect of 12-MTA on 5-HETE inhibition was also concentration dependent. The identity of the particular inhibitory 'spot' from preparative TLC was later identified by GC/MS, MS and NMR analysis and was confirmed to be 12-methyltetradecanoic acid (12-MTA).

Purification of sea cucumber derived 12-MTA:

12-MTA can be extracted from sea cucumber oils by the following methods:

Extraction of the sea cucumber gut tissues by supercritical $CO_2$ at pressures between 1000 psi and 2,000 psi at 60° C. at an effective flow rate suitable for the extraction vessel and volume, such extraction method suitable for isolation of the triglycerides of the starting oil material which contains approximately 50% 12-MTA. Subsequent further isolation of 12-MTA can be achieved by the saponification of the triglycerides by methods known to those in the lipid extraction arts; removal of glycerides; production of free fatty acids; crystallization of the saturated free fatty acids by subjecting the free fatty acids to −20° C. for 24 hours, and filtration of the saturated fatty acid crystals thus formed; repeated crystallization of said free fatty acids exhaustively; said procedure suitable for increasing the percentage of 12-MTA to approximately 50%. Further isolation can be accomplished by use of preparative column chromatography or preparative High Pressure Liquid Chromatography as is known in the lipid chemist's art. Also, a sea cucumber oil obtained by liquefied propane extraction of dry sea cucumber gut tissue as described in Collin, PCT/US99/01179 was further subjected to $CO_2$ extraction by entraining the sea cucumber oil in a substrate matrix (Hydromatrix® —Varian, Calif.) and contacting with a dense gas $CO_2$ at pressures between 1000 psi and 2,500 psi at a temperature of 60° C., and also drawing the lipid-bearing dense gas through a chamber filled with silica which entrained the carotenoid pigments of the lipid. The lipid so obtained was free of pigments, sterols and phospholipids.

12-MTA also can be extracted from sea cucumber oils that have been produced by any means of solvating dry or wet sea cucumber tissues and sequestering an extract, and sea cucumber tissues directly by means of supercritical carbon dioxide extraction, initially at pressures between 1000 psi and 2,500 at 60° C. at an effective flow rate suitable for the extraction vessel and volume, such extraction method suitable for isolation of the triglycerides of the starting material which contain approximately 25% by weight of 12-MTA.

It has been found that 12-MTA co-purifies initially with palmitoleic acid from a starting material of sea cucumber tissue or oils. Eicosapentaenoic acid (EPA) will also be extracted and partially purified with 12-MTA. These, and other sea cucumber-derived, or bacteria fatty acids do not interfere with the anti-inflammation and anti-cancer activities of a 12-MTA-bearing product. A preferred highly-purified 12-MTA preparation from a sea cucumber oil or tissue comprises 60% or more 12-MTA, palmitoleic acid between 10 and 30% myristic acid and eicosapentaenoic acid (EPA) between 10 and 40%.

Bacterial Sources for 12-MTA:

12-MTA can be obtained through cultivation of various bacteria. For an example, 12-MTA occurs in the fatty acid portion of Arthrobacter sp. CA 17-2 (FERM BP-4420) at approximately 50%. Other bacteria produce 12-MTA. The following strain of bacteria is given as only one example and is not meant to limit the selection of suitable bacteria for such isolation of 12-MTA. Marine bacteria can also be grown in methods similar to those described herein.

Cultivation of Arthrobacter sp. CA 17-2 (FERM BP-4420) as one example can produce a 12-MTA-rich lipid by the following method.

Stage I: Preparation of Seed Culture (a) In shake flasks

The seed culture medium 100 ml is taken in 500 ml wide mouth Erlenmeyer flask with presterilisation pH adjusted to 6.5. This is sterilized in an autoclave at 121° C. for 20 minutes, cooled and inoculated with spores from the culture Arthrobacter sp. CA 17-2 (FERM BP-4420). The flasks are incubated at 26° C. (+/−1° C.) for 48 hours at 240 r.p.m. on rotary shaker.

(b) In aspirator bottles 1 liter of a seed culture medium is taken with 0.4 ml of Desmophen® (Bayer AG) as antifoam in a 5 liter aspirator bottle. This is sterilized in an autoclave at 121° C. for 30 minutes, cooled and inoculated with spores from the Arthrobacter sp. CA 17-2 (FERM BP-4420). The bottles are mounted on a rotary shaker and incubated for 48 hours at 26° C. (+/−1° C.) at 240 r.p.m.

Stage II: Fermentation (a) Small scale 10 liter of the production medium with presterilisation pH adjusted to 6.5, with 4 ml Desmophen as antifoaming agent, in a 15 liter stainless steel fermenter, is sterilized in an autoclave at 121° C. for 36 minutes, cooled under sterile positive air pressure in water bath and seeded with 1% seed under aseptic conditions.

This is run with the following parameters:

| Temperature | 26–27° C. |
| --- | --- |
| Aeration | 1:0.6 to 0.8 vol/vol. of broth |
| | 6 to 8 liters per minute |
| Agitation | 160 rpm |
| Harvest Time | 66 hours |

(b) Large Scale

Ninety-five liters of the production medium in 150 liter fermenter with presterilization pH adjusted to 6.5 with 40 ml Desmophen or 270 liter medium in 390 liter fermenter with 75 ml Desmophen is sterilized in situ for 32 minutes at 121° C. and seeded with 1% seed under aseptic conditions. Exemplary methods are described by Moreau et al. (1995. Anal. Biochem. vol. 224, pp. 293–301) and Roth et al. (1995. Anal. Biochem. vol. 224, pp. 302–308, both references herein incorporated by reference).

Seeded volume: 110 liters in 150 liter fermenter; 280 liters in 390 liter fermenter This is run with the following parameters:

| Temperature: | 26°–27° C. |
| --- | --- |
| Aeration: | 1:0.6 to 0.8 vol/vol of broth |
| | for 110 liters: 60 to 80 lpm |
| | for 280 liters: 160 to 224 lpm (9 to 13 $nm^3$/hr) |
| Agitation: | 100–110 r.p.m. |
| Harvest time: | approximately 66 hours |

The harvested broth is centrifuged to separate the mycelium from the culture filtrate and then processed further.

Stage III: Isolation of 12-MTA-rich lipid

Culture broths are centrifuged to separate the culture filtrate from the mycelium. The culture filtrate (337 liters) is extracted once with ethyl acetate (245 liters). The mycelium (33.5 kg) is extracted with acetone (2×100 liters) and the extract is concentrated to 60 liters at 38° C. under reduced pressure (<100 torr). The concentrate is dried and extracted with liquefied $CO_2$ at supercritical pressure of approximately 1000 psi to 3,000 psi at 40° C. to obtain an oil which is approximately 50% 12-MTA. Purified 12-MTA can be purified and/or concentrated by methods known to those in the lipid purification arts. The crude bacterial lipid so obtained can also be utilized as a therapeutic for mammalian diseases in which lipoxygenase activation or activity contributes to the pathological condition.

EXAMPLE 1

Preparation of 12-MTA

A composition of matter derived from either sea cucumber tissue, and/or bacterial sources and/or bacterial fatty acids is produced by the selective removal (through liquefied $CO_2$, or other dense gas material known to those skilled in the extraction arts), of sterols, sterol esters, unsaturated fatty acids, phospholipids and glycolipids from the sea cucumber tissue, sea cucumber oil, or bacterial or bacterial oil starting material, and/or through preparative HPLC, column chromatography, or other means known to those in the lipid fractionation arts whereby the 12-MTA percentage is increased to more than 60% by weight. With sea cucumber derived 12-MTA, other fatty acids may include palmitoleic acid, eicosapentaenoic acid, myristic acid and others at percentages that do not detract from the activity of 12-MTA associated therewith.

EXAMPLE 2
Inhibition of Inflammation by a 60% 12-MTA Bearing Composition

By methods described above, a 12-MTA bearing compound is produced from sea cucumber lipid fractions that has a percentage of approximately 60% 12-MTA and is administered orally to an arthritis patient in need of inhibition of an overexpression of metabolites and isomers of 5-lipoxygenase. An effective dose of the 60% 12-MTA bearing compound, encapsulated in 500 milligram soft-gel capsules, is 40 milligrams per kilogram of body weight, taken daily by the patient. Arthritic inflammation symptoms will lessen within two weeks of such daily dosing.

EXAMPLE 3
In-vitro Cancer Cell Cytotoxicity of 12-Methyltetradecanoic Acid (12-MTA)

In order to better understand the biochemical mechanism of 12-MTA with respect to inhibition of tumor growth, the effect of 12-MTA on arachidonic acid metabolism and activation of peroxisome proliferator activated receptors (PPARs) was also studied.

1. Relative Cytotoxicity of 12-MTA to Tumor Cells

The relative cytotoxic activity of 12-MTA against human tumor cells was measured by means of a MTT assay. Human cell lines, including H1299, PC3, K562, A549, DU145, and HL60 were used. The $IC_{50}$. values of 12-MTA against these cell lines are shown in Table 1. The $IC_{50}$ values ranged from 18.15 µg/ml for H1299 cells to 33.1 µg/ml for K562 cells. Our results indicate the 12-MTA can effectively inhibit the growth of human tumor cells at relatively low concentrations.

TABLE 1

Cytotoxicity of 12-MTA against human tumor cells

| Cell lines | $IC_{50}$ (µg/ml) |
|---|---|
| H1299 | 18.15 |
| HL60 | 20.57 |
| A549 | 21.78 |
| PC3 | 30.12 |
| DU145 | 30.25 |
| K562 | 33.10 |

2. 12-MTA Causes Cell Death by Induction of Apoptosis a. Morphological Changes of PC3 Human Prostate Cancer Cells Treated with 12-MTA PC3 cells ($5\times10^5$) were plated in 35 mm dishes. After 24 hours, cells were treated with 24.2 µg/ml of 12-MTA in 0.1% DMSO. The cells were harvested at 30', 1, 2, 4 and 24 hours. Harvested cells were fixed with 2% paraformaldehyde plus 3% glutformaldehyde in 0.1% sodium cacodylate buffer, pH 7.3. Morphological changes were measured by scanning electron microscopy (SEM). Visual examination revealed that 12-MTA caused the cells to bleb and detach from the tissue culture plates as early as 1 hour after 12-MTA treatment. SEM results confirmed that cells exhibited apoptotic changes after 1-hour of exposure to 12-MTA with loosing cell surface cilia and vellum. At 2 hours, the detached cells showed significant apoptotic changes, such as cell roundness, budding of the cell surface, loosing of surface cilia, vellum and filapodia. These results demonstrate that 12-MTA causes adverse cell membrane changes, which is believed to contribute to its induction of cell death.

b. DNA Fragmentation Analysis

Figure 2:
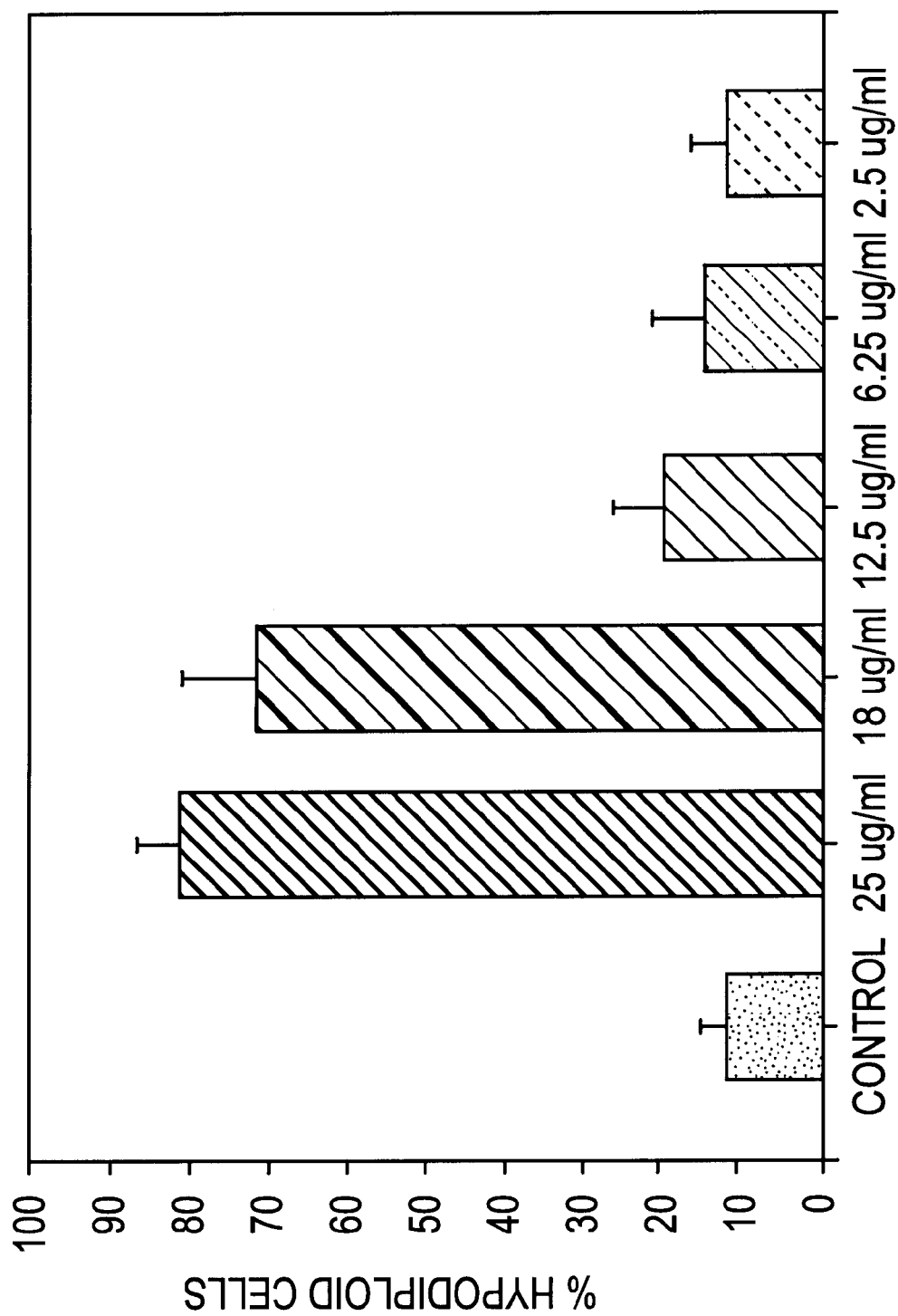
FIG. 2. Concentration dependent induction of apoptosis by 12-MTA in PC3 cells. Data are presented as mean +/− SD of three separated experiments.

To measure apoptosis directly, PC3 cells were treated with various concentrations of 12-MTA. Cell death by apoptosis was quantified by propidium iodide staining and FACS analysis. This technique measures cells with fragmented DNA, which appear as a population with hypodiploid DNA content (FIG. 2). 12-MTA induced concentration-dependent DNA fragmentation in PC3 cells. 12-MTA at 18.15 µg/ml significantly increased the percent of apoptotic cells up to 75% compared with normal non-treated cells. These results are consistent with the data obtained from SEM studies and strongly suggests that cell death caused by 12-MTA occurs by induction of apoptosis.

c. Caspase 3 Activation and PARP Cleavage

Figure 3:
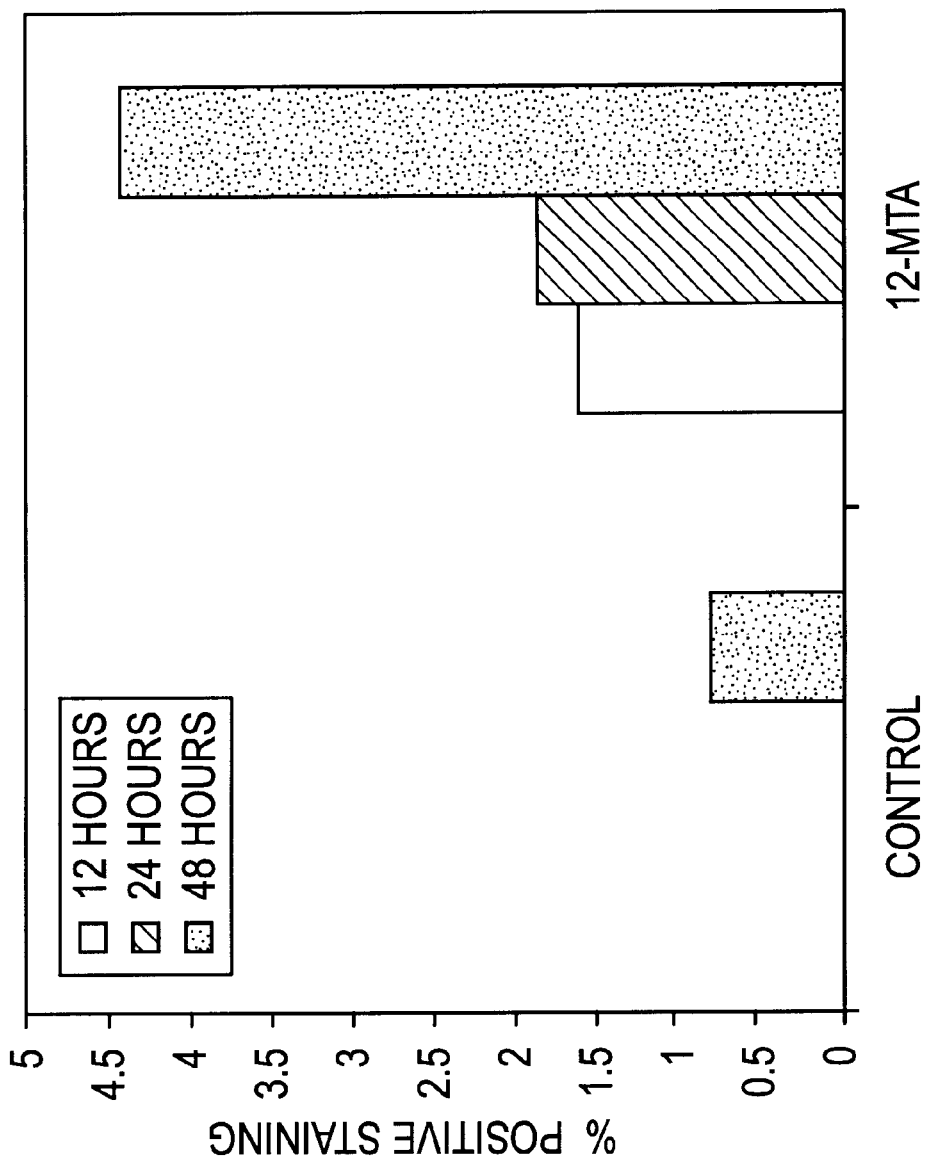
FIG. 3. The effect of 12-MTA on caspase 3 activity in PC3 cells.

Caspases are a family of aspartate-specific cysteine proteases that are required for apoptosis. The most familiar substrate of caspase is PARP, which is involved with regulation of chromatin structure during differentiation and DNA repair. The native PARP protein (Mr, 116,000) is cleaved by caspase 3 or caspase 7 to yield lower molecular weight fragments. To confirm that the induction of apoptosis by 12-MTA involves activation of caspases, we treated PC3 cells with 24.2 µg/ml of 12-MTA and measured PARP cleavage and caspase 3 activation at 24 and 48 hours. The data show that 12-MTA treated cells displayed prominent PARP cleavage. Direct measurement of caspase 3 activation confirmed that 12-MTA can activate caspase 3 and that the activation was time-dependent (FIG. 3).

3. Inhibition of 5-lipoxygenase Activity

12-MTA in rat leukemia (RBL-1) cells were examined. Cells were treated with 12-MTA (5 to 100 µg/ml) for 5 minutes at 37° C. followed by addition of A23187 (1 mM) and arachidonic acid (125 µM). Then the eicosanoids were extracted with hexane:ethyl acetate and analyzed by Multiple Reaction Monitoring in a tandem mass spectrometer (LC/MS/MS). Among seven eicosanoid metabolites, including $PGE_2$, $LTB_4$, 5-, 8-, 11-, 12-, and 15-HETEs, reduced production of 5-HETE and $LTB_4$ in 12-MTA treated cells was observed. The $IC_{50}$ for inhibition of both 5-HETE and $LTB_4$ was approximately 25 µg/ml (FIG. 1). The inhibitory activity of 12-MTA on production of 5-HETE and $LTB_4$ was concentration-dependent. This study further confirmed that 12-MTA is a 5-lipoxygenase inhibitor. 12-MTA, at 100 µg/mL, inhibited production of 12-HETE by 25% growth.

4. Activation of Peroxisome Proliferator-Activator Receptor (PPAR)

Peroxisome proliferator-activated receptors (PPAR) represent a family of steroid hormone receptors in a superfamily mainly involved with lipid metabolism. Recently, high levels of PPAR-γ were reportedly expressed in prostate cancer tumor and activation of PPAR-γ was associated with nonapoptotic cell death induced by some PPAR-γ ligands. Many unsaturated long chain fatty acids and their metabolites have been demonstrated to act as ligands via binding to specific PPAR types. We have examined the effects of 12-MTA on activation of PPAR-γ in DU145 and PC3 cells. Cells were treated with 24.2 µg/ml of 12-MTA in serum-free media. After 24 hours, cells were harvested and expression of PPAR-γ was detected by immunoblot with or without blocking peptide. Preliminary data showed that 12-MTA only slightly increased the expression of PPAR-γ in both cell lines comparing with controls. These data suggest that 12-MTA may not induce cell death through direct interaction with PPAR receptors.

In vitro results show that 12-MTA, at relatively low concentrations, can inhibit the growth of a variety of human tumor cells. Cell death caused by 12-MTA occurs through induction of apoptosis which can be detected as early as 2 hours after exposure of cells to this particular saturated fatty acid. Further investigation of the effect of 12-MTA on alteration of LOX and COX metabolites and activation of proximal proliferation receptors (PPAR) has shown that this compound can selectively inhibit 5-lipoxygenase metabolites, but does not appear to serve as an effective ligand for PPAR-γ.

What is claimed is:

1. A composition of matter comprised of at least 60% w/w 12-MTA, between about 10% and 40% w/w eicosapentaenoic acid (EPA, 20:5) and between about 10% and 30% w/w palmitoleic acid (16:1) derived from sea cucumber lipids.

2. A composition of claim 1, wherein the composition is obtained by selective removal from sea cucumber lipids of sterols, sterol esters, phospholipids, pigments, and glycolipids through extraction by supercritical $CO_2$, polar co-solvents or preparative HPLC.

* * * * *